(12) United States Patent
Vazquez Alvarez et al.

(10) Patent No.: US 10,130,730 B2
(45) Date of Patent: Nov. 20, 2018

(54) WAX MELT COMPOSITIONS HAVING INCREASED THERMAL STABILITY

(71) Applicant: The Dial Corporation, Scottsdale, AZ (US)

(72) Inventors: Terannie Vazquez Alvarez, Gilbert, AZ (US); Tyler Mikkelsen, Scottsdale, AZ (US); Kevin Hafer, Chandler, AZ (US); Debra A. Park, Mesa, AZ (US)

(73) Assignee: Henkel IP & Holding GmbH (DE)

( * ) Notice: Subject to any disclaimer, the term of this patent is extended or adjusted under 35 U.S.C. 154(b) by 423 days.

(21) Appl. No.: 14/982,983

(22) Filed: Dec. 29, 2015

(65) Prior Publication Data

US 2017/0182198 A1    Jun. 29, 2017

(51) Int. Cl.
| | |
|---|---|
| *A61L 9/03* | (2006.01) |
| *A61L 9/012* | (2006.01) |
| *A61K 9/00* | (2006.01) |
| *C11C 5/00* | (2006.01) |
| *C08L 91/06* | (2006.01) |

(52) U.S. Cl.
CPC ............ *A61L 9/03* (2013.01); *A61K 9/007* (2013.01); *A61L 9/012* (2013.01); *C08L 91/06* (2013.01); *C11C 5/00* (2013.01); *C11C 5/002* (2013.01); *C11C 5/008* (2013.01)

(58) Field of Classification Search
None
See application file for complete search history.

(56) References Cited

U.S. PATENT DOCUMENTS

| | | | | |
|---|---|---|---|---|
| 3,843,312 A | * | 10/1974 | Easterday | ............... C08L 91/06 431/288 |
| 4,758,432 A | * | 7/1988 | Yeung | ...................... A61K 8/31 514/763 |
| 2009/0053268 A1 | | 2/2009 | Depablo et al. | |
| 2010/0212214 A1 | | 8/2010 | Boneng et al. | |

FOREIGN PATENT DOCUMENTS

| | | |
|---|---|---|
| CN | 1531585 A | 9/2004 |
| WO | 0183656 A1 | 11/2001 |
| WO | 2004044112 A1 | 5/2004 |
| WO | WO-2004044112 A1 * | 5/2004 ............. C11C 5/002 |

OTHER PUBLICATIONS

Biscox, wax—weather forecasters (Year: 1931).*

* cited by examiner

*Primary Examiner* — Melvin C. Mayes
*Assistant Examiner* — Stefanie J Cohen
(74) *Attorney, Agent, or Firm* — Bojuan Deng (57) ABSTRACT

Wax melt compositions loaded with a volatile agent for release therefrom having beneficial performance properties and behavior are disclosed and described. In certain embodiments, such was melt compositions can include a wax component, a releasable volatile agent, a first inorganic thickener that is hydrophobically modified, and a second inorganic thickener.

19 Claims, 2 Drawing Sheets

WAX MELT COMPOSITIONS HAVING INCREASED THERMAL STABILITY

BACKGROUND

Scented candles have been used to disseminate a fragrance for a variety of reasons such as air freshening and aromatherapy. Some candles have a wick and are intended to produce a flame while others may be wickless and heated in a container with an external, even flameless heating source. Such candles typically include a fragrance oil dispersed throughout the wax for release when the wax is heated.

BRIEF DESCRIPTION OF THE DRAWINGS

For a fuller understanding of the nature and advantage of the present invention, reference is being made to the following detailed description of preferred embodiments and in connection with the accompanying drawings, in which.

DESCRIPTION OF EXAMPLE EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a wax" includes a plurality of such waxes.

As used herein, a "volatile agent," refers to an agent or substance with a high tendency to vaporize and remain a vapor at ambient temperatures. For example, most fragrance oils vaporize over time when exposed to the open air. Those of ordinary skill in the art will recognize that different substances can have different degrees of volatility, even under the same or similar conditions.

As used herein, an "effective amount," of an agent, component, or ingredient, can be an amount that is sufficient to achieve or provide a desired or expected outcome or effect. For example, if it is desired to minimize viscosity loss of a wax composition upon heating, then an effective amount of a thickener would be at least the minimum amount required in order to maintain the wax's viscosity up to a certain temperature.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this specification it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Objects described herein as being "adjacent to" each other may be in physical contact with each other, in close proximity to each other, or in the same general region or area as each other, as appropriate for the context in which the phrase is used.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Wax compositions, such as candles and wax melts, can be effective vehicles for releasing a releasable volatile agent into a surrounding area. However, many wax compositions used with electrical and candle-heated warmers have a low viscosity when heated and are prone to splashing. Further, wax compositions can typically only hold small amounts of releasable volatile agents, such as fragrances, without experiencing syneresis. Syneresis refers to the separation of a liquid component from the solid wax mass at ambient temperature. Thus, where the releasable volatile agent exceeds the loading or holding capacity of the wax component, the wax composition will begin to experience syneresis (i.e. the releasable volatile agent will exude from the wax component). Additionally, with respect to wax melt compositions, after a heating and cooling cycle where the wax melt is at least partially melted on a heated surface or dish, the wax melt composition can become difficult to remove from the surface.

Accordingly, wax melt compositions are described herein that can overcome some of the typical challenges of traditional wax compositions. For example, in one embodiment the wax melt composition can include a wax component, a releasable volatile agent, a first inorganic thickener that is hydrophobically modified, and a second inorganic thickener.

The wax component can include a variety of suitable waxes or blends of waxes. In some examples, the wax can include a vegetable wax, an animal wax, a synthetic wax, a mineral wax, a petroleum wax, or combinations thereof. Some non-limiting examples of vegetable waxes can include: soy wax, bayberry wax, carnauba wax, candelilla wax, palm wax, arrayan wax, sugar cane wax, castor wax, cotton wax, tallow tree wax, rice bran wax, ouricury wax, jojoba wax, esparto wax, raffia wax, or combinations thereof. Some non-limiting examples of animal waxes can include: beeswax, lanolin wax, ghedda wax, spermaceti wax, shellac wax, Chinese wax, or combinations thereof. Some non-limiting examples of synthetic waxes can include: polyethylene wax, Fischer-Tropsch wax, chemically modified vegetable wax, chemically modified animal wax, chemically modified mineral wax, chemically modified petroleum wax, or combinations thereof. Some non-limiting examples of mineral waxes can include: peat wax, ceresin wax, montan wax, ozocerite wax, or combinations thereof. Some non-limiting examples of petroleum wax can include: paraffin wax, slack wax, scale wax, microcrystalline wax, or combinations thereof.

While a variety of waxes can be used in the wax melt compositions, in some examples the wax component can include a paraffin wax, a blend of a paraffin wax and at least one non-paraffin wax, or a blend of paraffin waxes.

Chain length can also be important in the design of wax melt compositions. Some general classifications of waxes can include paraffin waxes, intermediate waxes, and micro waxes. Paraffin waxes typically have linear chains from C18 to C40. However, intermediate waxes have branched chains from C25 to C60. Additionally, micro waxes can have a complex, branched structure with chains from C25 to C85. Waxes with longer chain lengths typically have higher melting points and waxes with shorter chain lengths typically have lower melting points. However, branched chains can decrease the melting point of waxes.

Due to the complexity and diversity of wax chain lengths, waxes have often been defined by their melting points. For example, waxes that melt at about 53° C. or less can be classified as low-melting waxes, waxes that melt from about 53-63° C. can be classified as mid-melting waxes, and waxes that melt above 63° C. can be classified as high-melting waxes. In some cases, low-melting waxes can have chain lengths of about C28 to C30 or less, mid-melting waxes can have chain lengths of about C28 to C30 to about C34 to C36, and high-melting waxes can have chain lengths of about C34 to C36 or above.

Because of their differing natures, it can be beneficial to blend different types and chain lengths of waxes to achieve a wax composition with preferred properties and performance characteristics. For example, in some cases, high-melting waxes can provide greater loading and retention of releasable volatile agents. However, in some cases, low-melting waxes can provide quicker release of the releasable volatile agents. Thus, in one example, the wax component can have a blend of low-melting waxes and high-melting waxes. In another example, the wax composition can have a blend of low melting waxes and mid-melting waxes. In another example, the wax composition can have a blend of mid-melting waxes and high-melting waxes. In yet another example, the wax can be a high-melting wax or blend of high-melting waxes. In one example, the wax can be a mid-melting wax or blend of mid-melting waxes. In one example, the wax can be a low-melting wax or blend of low-melting waxes.

The wax component of the current composition can have a variety of chain lengths. In one example, the wax component can include a wax or blend of waxes having an average chain length from about C15 to about C80. In another example, the wax component can include a wax or blend of waxes having an average chain length from about C18 to about C60. In another example, the wax component can include a wax or blend of waxes having an average chain length from about C20 to about C40. In a further example, the wax component can include a wax or blend of waxes having an average chain length from about C20 to about C30.

In one example, the wax component can be present in the composition in an amount from about 5 wt % to about 95 wt %. In another example, the wax component can be present in the composition in an amount from about 50 wt % to about 95 wt %. In another example, the wax component can be present in the composition in an amount from about 70 wt % to about 95 wt %. In another example, the wax component can be present in the composition in an amount from about 80 wt % to about 90 wt %.

As previously discussed, a releasable volatile agent can be included in the composition with the wax component. The releasable volatile agent can be any releasable volatile agent that can be suitably included in and released from a wax melt composition. Volatile agents can be selected in order to provide specific products for specific purposes, or having specific properties. Examples of releasable volatile agents can include, without limitation, a fragrance, a pesticide, a pest repellant, an herbicide, a therapeutic or medicinal agent, or combinations thereof.

In one example, the releasable volatile agent can be a fragrance. Fragrances are well known in the art and the fragrances used in the current compositions can include any suitable fragrance or combination of fragrances. For example, fragrances can include any suitable perfume, cologne, fragrance oil, essential oil, the like, or combinations thereof. The fragrance can be formulated to have top notes, middle notes, bottom notes, and combinations thereof. In short, there are many fragrances and fragrance combinations that can be used in the current composition.

In another example, the releasable volatile agent can be a pest repellent. Pest repellents are generally known in the art and can include any suitable pest repellent. In some examples, the pest repellent can include an essential oil, such as citronella oil, peppermint oil, basil oil, lemongrass oil, cinnamon oil, pine oil, juniper oil, oregano oil, grapefruit oil, lemon oil, the like, and combinations thereof. Pest repellents can also include N,N-Diethyl-meta-toluamide (DEET), picaridin, 3-[N-Butyl-N-acetyl]-aminopropionic acid ethyl ester (IR3535), dimethyl carbate, ethylhexanediol, dimethyl phthalate, metofluthrin, indalone, tricyclodecenyl allyl ether, the like, and combinations thereof. There are a number of other pest repellents that can be include in the current compositions that are known in the art and the current compositions.

Because wax melt compositions are typically prepared at elevated temperatures, one consideration in selecting a suitable releasable volatile agent can be the flash point of the releasable volatile agent. In some embodiments, releasable volatile agents can have a low flash point. However, in some cases, it can be beneficial to use a releasable volatile agent with a somewhat elevated flash point. In some examples, the releasable volatile agent can have a flash point of at least 140° C. In other examples, the releasable volatile agent can have a flash point of at least 160° C. In further examples, the releasable volatile agent can have a flash point of at least 170° C. In yet other examples, the releasable volatile agent can have a flash point of at least 180° C.

In some examples, the releasable volatile agent can be present in the composition in an amount from about 0.01 wt % to about 30 wt %. In one example, the releasable volatile agent can be present in the composition in an amount from about 0.5 wt % to about 15 wt %. In another example, the releasable volatile agent can be present in the composition in an amount from about 1 wt % to about 10 wt %. In yet another example, the releasable volatile agent can be present in the composition in an amount from about 3 wt % to about 8 wt %

In addition to the wax component and the releasable volatile agent, the wax melt composition can include a combination of inorganic thickeners. The inorganic thickeners can include a variety of inorganic thickeners, including modified inorganic thickeners. A modified inorganic thickener can be modified to include a variety of moieties, including both hydrophobic and hydrophilic moieties. Generally, unmodified inorganic thickeners can be hydrophilic. Nonetheless, it can be advantageous to modify these inorganic thickeners to include hydrophilic moieties. It can also be advantageous to modify inorganic thickeners to include hydrophobic moieties. These modifications can be made for a variety of reasons, such as to increase the solubility of one or more components, to provide greater thickening properties, to impart specific functional characteristics to the product, and the like.

More specifically, in some examples, the first inorganic thickener can be a hydrophobically modified inorganic thickener. Non-limiting examples of hydrophobically modified inorganic thickeners can include a silica, a silicate, a clay, fumed or non-fumed alumina, fumed or non-fumed titanium dioxide, the like, or combinations thereof. In one specific example, the first inorganic thickener can be a silica. In another example, the silica can be a precipitated silica or a fumed silica.

The first inorganic thickener can be modified by treatment with a polydimethylsiloxane (PDMS), a methacrylsilane, a dimethyldichlorosilane, an octamethylcyclotetrasiloxane, an alkylsilane, an alkoxysilane, a hexamethyldisiloxane, a hexamethyldisilazane, a silicone oil, an aminosilane, a silanol, or combinations thereof. In one specific example, the first inorganic thickener can be a fumed silica that has been modified by treatment with PDMS.

The first inorganic thickener can be present in the composition in an amount from about 0.01 wt % to about 20 wt %. In one example, the first inorganic thickener can be present in the composition in an amount from about 1 wt % to about 10 wt %. In another example, the first inorganic thickener can be present in the composition in an amount from about 3 wt % to about 8 wt %.

The second inorganic thickener can be a variety of inorganic thickeners. Non-limiting examples can include a silica, a silicate, a clay, fumed or non-fumed alumina, fumed or non-fumed titanium dioxide, hydrated magnesium, calcium carbonate, the like, or combinations thereof. The second inorganic thickener can be modified or unmodified. In one example, the second inorganic thickener is hydrophobically modified and is different from the first inorganic thickener. In one example, the second inorganic thickener is hydrophilically modified.

In one specific example, the second inorganic thickener can be a silica. In some examples, the silica can be a precipitated silica or a fumed silica. In one example, the silica can be modified by treatment with a PDMS, a methacrylsilane, a dimethyldichlorosilane, an octamethylcyclotetrasiloxane, an alkylsilane, an alkoxysilane, a hexamethyldisiloxane, a hexamethyldisilazane, a silicone oil, an aminosilane, a silanol, or combinations thereof. In one specific example, the silica can be modified by treatment with dimethyldichlorosilane. The second inorganic thickener and the first inorganic thickener are different.

In some examples, the second inorganic thickener is present in the composition in an amount from about 0.01 wt % to about 15 wt %. In another example, the second inorganic thickener is present in the composition in an amount from about 0.1 wt % to about 10 wt %. In another example, the second inorganic thickener is present in the composition in an amount from about 0.5 wt % to about 8 wt %.

Additionally, the ratio of inorganic thickeners in the wax melt composition can be an important aspect of the current composition, as will be described more fully below. In some examples, the first inorganic thickener and the second inorganic thickener can be present in the composition at a weight ratio of from 1:1 to 8:1, or from 1:1 to 6:1, or from 2:1 to 4:1.

In addition to the first and second inorganic thickeners, the wax melt composition can also include a solubilizing agent. A variety of solubilizing agents can be used, such as polyols, surfactants, or combinations thereof. Some non-limiting examples of suitable polyols can include polymeric polyols, monomeric polyols, sugar alcohols, or combinations thereof. Polymeric polyols can include polyethylene glycol, polypropylene glycol, polyvinyl alcohol, the like, or combinations thereof. Monomeric polyols can include propylene glycol, glycerol, butylene glycol, ethylene glycol, the like, or combinations thereof. Sugar alcohols can include maltitol, sorbitol, mannitol, inositol, xylitol, arabitol, erythritol, threitol, the like, or combinations thereof. Suitable surfactants can include a polysorbate, a sorbitan ester, an alkyl sulfate, an alkyl carboxylate, or combinations thereof.

The solubilizing agent can be present in the composition in an amount from about 0.01 wt % to about 10 wt %. In one example, the solubilizing agent can be present in an amount from about 0.5 wt % to about 8 wt %. In another example, the solubilizing agent can be present in an amount from about 3 wt % to about 7 wt %.

In some embodiments, the wax melt compositions can be included in a system for volatilizing a releasable volatile agent. Such a system can include a heat source, for example, an electric heater, a resistive heater, or a candle or other source of open flame. In some examples, the heat source can provide a heating temperature of at least 55° C., or at least 90° C., or at least 105° C., or at least 120° C.

In most embodiments, a heating receptacle can be associated with the heat source. For example, the heating receptacle can be a dish or other receptacle that is positioned above a candle or other burner. In another aspect, the receptacle can be a dish or other receptacle that is adapted for direct placement on a burner or hot-plate. In another aspect, the receptacle can be thermally connected to an electrical or resistive heat source via wires or other suitable mechanism.

Some systems can also include a container for the wax melt composition. In one example, the container can be a gas-tight container. The container can be made of a variety of materials, such as polyethylene, polypropylene, polystyrene, ethylene vinyl alcohol, paperboard, cellophane, glass, metals such as titanium and aluminum, metal oxides such as alumina, metal alloys such as stainless steel, or combinations thereof. When the container comprises a material that is not heat resistant, the wax melt composition will be removed from the container and separately used with the heat source. However, in cases where the container is heat resistant, the container may be used directly in connection with the heat source with the wax melt composition remaining therein.

The present disclosure also encompasses a variety of methods associated with wax melt compositions. For example, a method of minimizing the splash potential of a wax melt composition during a heating event is described. Furthermore, a method of minimizing a decrease in viscosity of a wax melt composition during a heat event is described. In such methods, an effective amount and weight ratio the first inorganic thickener and the second inorganic thickener can be included in the wax melt composition. The effective amounts and weight ratios of the inorganic thickeners are described above in the compositional embodiments and examples.

As previously mentioned, the ratio of inorganic thickeners in the wax melt composition can be an important aspect of the current compositions. For example, some ranges and amounts of the first and second inorganic thickeners can provide increased thermal stability of the wax compositions and can even increase the chemical compatibility of various additives, including the releasable volatile agent. In some cases, the combination of inorganic thickeners in the specified ratios can change both the ambient and the melting properties of the wax melt composition. For example, a wax melt composition without the combination of inorganic thickeners will typically melt to a completely fluid state during a heating event, but the current wax melt compositions can retain a higher level of viscosity and merely soften to a semi-fluid or minimally-fluid state under the same or similar heating event. This can minimize or reduce the splash potential of the wax melt composition during a heating event as compared to a wax melt composition without the combination of thickeners and provide increased safety and convenience for a consumer or user.

In some cases, the combination of inorganic thickeners can interact with each other directly or indirectly via the other components of the wax composition. Where this happens, the combination of inorganic thickeners can form a three-dimensional matrix within the wax composition that provides increased stability and thickening of the wax composition.

Thus, when an appropriate amount and weight ratio of inorganic thickeners is included in the composition, the viscosity of the composition can be maximized and the splash potential of the wax melt composition can be minimized during a heating event as compared to a wax composition that does not include the combination. In some examples, the higher viscosity of the wax melt composition at elevated temperatures can minimize or decrease the flow of the wax melt composition, and correspondingly decrease the splash potential of the composition. Splash potential can include the potential of any part of the wax composition to splash if bumped, agitated, spilled, leaked, tipped, or the like. In some cases, a wax melt composition having effective amounts of the first and second inorganic thickeners in an appropriate weight ratio of can remain in a heated dish without splashing or spilling even when inverted, where other wax compositions are typically fluid and pour out of the heated dish.

The heating event described in this method can include heating the wax melt composition to a temperature of at least 55° C., or at least 90° C., or at least 105° C., or at least 120° C. At these temperatures, a wax melt composition including effective amounts and weight ratios of the first and second inorganic thickeners as previously described can have a markedly reduce the splash potential.

In another embodiment, a method of minimizing syneresis of the releasable volatile agent in the wax melt composition is described. In this method, an effective amount and weight ratio of the first inorganic thickener and the second inorganic thickener can be included in the wax melt composition. In some examples, the combination of the first and second inorganic thickeners can increase the holding or loading capacity of the wax melt composition for the releasable volatile agent so that syneresis is minimized or eliminated. In one example, the combination can effectively increase the holding or loading capacity of the wax melt composition by at least 10%, 15%, or even 20% as compared to a wax composition without the combination of the first and second inorganic thickeners. As a non-limiting example, in some cases, where a wax melt composition without the combination of inorganic thickeners can effectively hold 3 wt % of a particular fragrance without experiencing syneresis, a wax melt composition that includes the combination of inorganic thickeners can effectively hold at least 3.3 wt %, 3.45 wt %, or even 3.6 wt % of the same fragrance, without experiencing syneresis.

In some examples, a wax melt composition that includes an effective amount of each of the first and second inorganic thickeners in an appropriate weight ratio, as described above, can hold a releasable volatile agent in amounts of at least 8 wt %, 10 wt %, 15 wt %, or even 20 wt % without experiencing syneresis. The amount of releasable volatile agent that a wax melt composition can hold, with or without the combination of thickeners, can be affected by a number of factors. Such factors can include the molecular weight, molecular configuration, functionality, polarity, pH, and other aspects of the releasable volatile agent.

In addition to the foregoing, invention embodiments encompass methods of extending the useful life of a loaded or scented wax melt composition. In one such method an effective amount and weight ratio of the first inorganic thickener and the second inorganic thickener can be included in the wax melt composition. In an effective amount and weight ratio, the combination of inorganic thickeners can minimize a throw period of the releasable volatile agent (i.e. a window during which the volatile agent is thrown or released from the wax composition in significant amounts with the application and removal of heat). For example, a typical wax melt composition will completely liquefy during a heating event. In contrast, by including an effective amount and weight ratio of the first and second inorganic thickeners in the wax melt composition, the composition can maintain a viscosity and not completely liquefy during a heating event. This can provide more control over release of the releasable volatile agent. In some examples, the increased viscosity of the wax melt composition can allow the wax melt composition to harden (i.e. re-solidify) or thicken more quickly and thus more quickly slow or stop the throw of the volatile agent and entrap the volatile agent within the body of the composition. This can shorten the window or throw period during which the releasable volatile agent can escape, or escape in significant amounts, from the wax melt composition or be released from the composition.

In some aspects, the throw period can include a period of heating and a period of cooling, thickening, or re-solidification. The period of heating is generally determined by a user. The cooling period can begin when heat is no longer added to the wax melt composition and can conclude when the wax melt composition has sufficiently cooled to thicken, re-solidify, or harden the composition to a point where escape or release of the releasable volatile agent is minimized or substantially arrested. In some limited cases, this will require the wax composition to cool to ambient temperature. However, in many cases, sufficient hardening or thickening of the wax composition will occur a temperature well above ambient temperature. In some examples, the cooling period can be 30 minutes or less, 20 minutes or less, 15 minutes or less, or even 10 minutes or less.

In additional embodiments, methods of minimizing adherence of a wax melt composition to an adjacent surface following heating and cooling of the wax melt composition against the surface are described. In such methods an effective amount and weight ratio of the first inorganic thickener and the second inorganic thickener can be included in the wax melt composition. The combination of the first and second inorganic thickeners can reduce adherence of the wax melt composition to the adjacent surface as compared to a wax melt composition without the combination of the first and second inorganic thickeners. This can facilitate rapid exchange of one wax melt composition for another. In contrast, many products currently on the market become adhered to the adjacent surface during the heating and cooling cycle, making the composition challenging to remove and replace.

In some examples, the combination of inorganic thickeners can increase the overall cohesion of the wax melt composition, even at elevated temperatures. This can reduce or minimize the flow of the composition at elevated temperatures, increase the overall integrity of the wax melt composition, and minimize the adhesion of the composition to adjacent surfaces. In some examples, the inorganic thickeners can interact with each other and/or the wax component(s) to impart increased cohesiveness to the wax melt composition.

Accordingly, the combination of inorganic thickeners in the wax melt composition can minimize adherence of the composition to a variety of surfaces, including ceramic surfaces, stainless steel surfaces, glass surfaces, polymeric surfaces, and the like. In one specific example, the adjacent surface can be a ceramic surface, a glass surface, or a combination thereof. The adjacent surface can be heated to any suitable temperature, such as at least 55° C., or at least 90° C., or at least 105° C., or at least 120° C. Even after extreme heating events, a wax melt composition that includes an effective amount and weight ratio of the first and second inorganic thickeners can minimally adhere to an adjacent surface on which it was heated and cooled.

Methods of making wax melt compositions, such as a syneresis-resistant and/or splash-resistant wax melt composition, can include providing a molten wax composition and admixing a syneresis-reducing or splash-reducing amount of a combination of inorganic thickeners therewith. In one embodiment, the combination can include a first inorganic thickener that is hydrophobically modified and a second inorganic thickener. The method can also include admixing an amount of a releasable volatile agent, such as a fragrance, in the molten wax composition. The method also includes solidifying the wax melt composition. In some embodiments, the wax component can be melted at a temperature from about 60° C. to about 90° C. Additionally, a wax melt composition with additional thickeners can be mixed in a high-shear mixer at rotational velocities of 1000 revolutions per minute (rpm) or more.

In one specific example, a paraffin wax can be added to a mixing vessel and heated to 60-90° C. Once melted a fragrance can be added to the molten wax and mixed. To this composition Aerosil® R202, a fumed silica that has been hydrophobically modified with PDMS (commercially available from Evonik), can be added and mixed at a high shear velocity of about 1100 rpm. Subsequently, Aerosil® R972, a fumed silica that has been hydrophobically modified with dimethyldichlorosilane (commercially available from Evonik), can also be added and mixed at a high shear velocity of about 1100 rpm. The composition can then be poured into a container, mold, or other receptacle to cool and solidify.

EXAMPLES

The following examples include a number of tables that list ingredients by their tradenames. For the purpose of clarity, those ingredients are described more fully here. Specifically, Aerosil® R202 is a fumed silica that has been hydrophobically modified with PDMS, Aerosil®300 is a hydrophilic fumed silica, Aerosil® R972 is a fumed silica that has been hydrophobically modified with dimethyldichlorosilane, and Sipernat®500LS is a precipitated silica. Each of these products is commercially available from Evonik.

Example 1—Combination of Inorganic Thickeners Improves Viscosity

A variety of wax melt compositions were prepared with different thickeners and solubilizing agents. The objective was to prepare a wax melt composition that had sufficient viscosity during a heating event to minimize the splash potential of the composition. All compositions included from 3-5 wt % of a fragrance and from 70-90 wt % paraffin wax (Parafflex®4826A, commercially available from The International Group). Each test formulation was heated to approximately 90° C. for a period of 30-60 minutes in a ceramic dish. After heating, each composition was visually inspected and agitated to determine general viscosity improvements over standard wax compositions without any solubilizing agents or thickeners. Table 1 illustrates some representative examples of compositions that exhibited increased viscosity.

TABLE 1

| Prototype | Aerosil® R202 | Aerosil® 300 | Aerosil® R972 | SIPERNAT® 500LS | PG | CaCO3 | Clay | Performance Thicker Viscosity |
|---|---|---|---|---|---|---|---|---|
| 1A | 5.50% | | 2.00% | | 5.00% | | | +++ |
| 5A | 5.50% | | 2.25% | | 5.00% | | | +++ |
| 2D | 5.50% | | 2.00% | | 5.00% | | 0.50% | +++ |
| 2F | 5.50% | | 1.50% | | | | | +++ |
| 4A | 5.50% | | 1.00% | | 5.00% | | | ++ |
| 9K | | 6.00% | | | 5.00% | | | ++ |
| 10L | 5.50% | | | | 5.00% | | | ++ |
| CC1 | | | | | 5.00% | 8.00% | 4.25% | ++ |
| 2A | 5.50% | | 0.75% | | 5.00% | | | + |
| 1B | | | 2.50% | | 5.00% | 8% | | + |
| 5G | | | | 6.00% | 5.00% | | | + |
| 7E | | | 5.50% | | 5.00% | | | + |
| 14P | | | | 5.00% | 5.00% | | | + |

It is noted that Table 1 only represents a small fraction of the formulations and components tested. Yet, as can be seen from the results of these representative examples, a variety of inorganic thickeners can significantly improve the viscosity of wax melt compositions at elevated temperatures. Based on the results of this study, a combination of hydrophobically-modified fumed silicas can provide excellent thickening properties. Two representative examples of hydrophobically modified silicas are listed in Table 1, namely Aerosil® R202 and Aerosil® R972 (both commercially available from Evonik). While this particular combination is used for illustrative purposes, there are a number of hydrophobically modified fumed silicas or other inorganic thickeners that can be used in combination to achieve thickening of wax melt compositions.

Of note, prototype 10L included only the Aerosil® R202 as an inorganic thickener and prototype 7E included only the Aerosil® R972 as an inorganic thickener. While each one separately was effective at thickening their respective formulations, the combination of both Aerosil® R202 and Aerosil® R972 provided superior thickening. In comparison, as seen in prototype 1B, the Aerosil® R972 in combination with calcium carbonate also improved the viscosity of the formulation, but not to the same extent as the combination of hydrophobically-modified fumed silicas. Further, addition of a solubilizing agent, such as propylene glycol (PG), did not appear to adversely affect the viscosity of the wax compositions that included a combination of hydrophobically-modified fumed silicas.

Images of the top-performing prototypes listed in Table 1 (1A, 5A, 2D, 2F) are represented as FIGS. 1A-1D, respectively. As can be seen in FIGS. 1A-1D, these compositions exhibited improved viscosity and decreased or minimized flow at temperatures of about 90° C. In contrast, typical wax melt compositions become completely fluid at this temperature. Thus, exemplary wax melt compositions similar to those illustrated Table 1 can decrease the splash potential of wax melt compositions, especially those that include a combination of inorganic thickeners, such as hydrophobically-modified fumed silicas. In particular, a weight ratio of Aerosil® R202 to Aerosil® R972 at about 2:1 to about 8:1 appeared to be effective at thickening wax melt formulations. More particularly, a weight ratio of Aerosil® R202 to Aerosil® R972 at about 2:1 to about 4:1 appeared to be very effective at thickening wax melt compositions.

Example 2—Inorganic Thickeners Improve Ease of Release

Figure 1A:
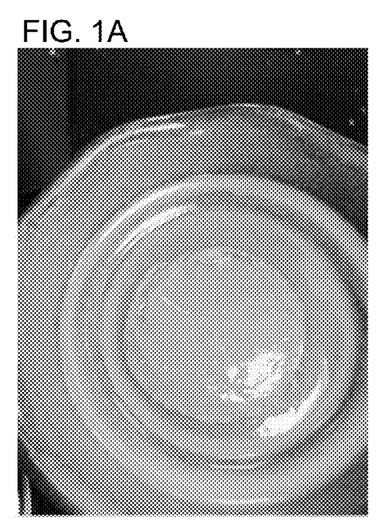
FIGS. 1A-1D show example wax melt compositions that exhibit various viscosities during a heating event.
Figure 1B:
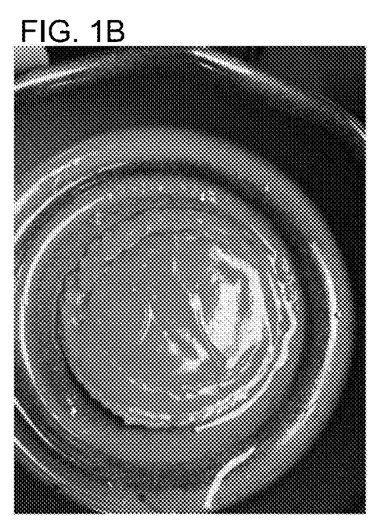
Figure 1C:
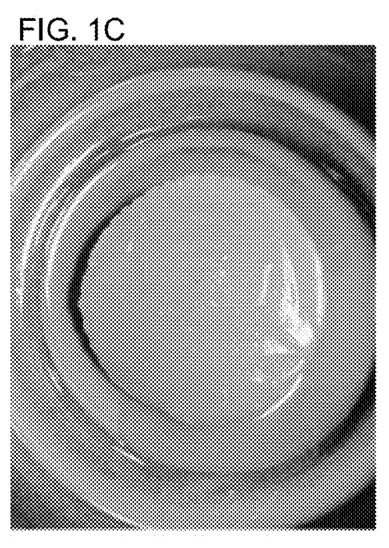
Figure 1D:
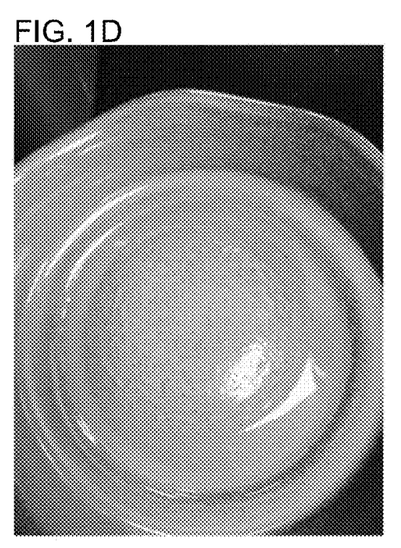
Figure 2A:
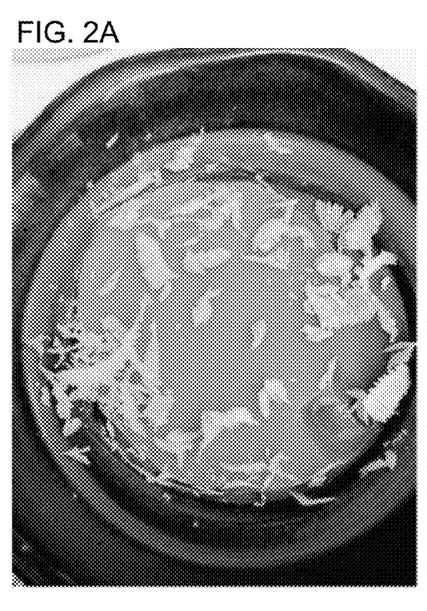
FIG. 2A shows an example wax melt composition that has been heated and cooled and adhered to the ceramic dish in which it was heated.
Figure 2B:
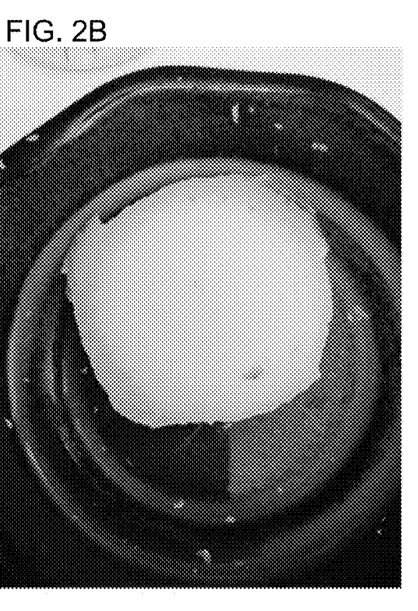
FIG. 2B shows an example wax melt composition that has been heated and cooled and did not adhere to the ceramic dish in which it was heated.

In connection with Example 1, the same wax melt formulations were evaluated to determine how easy they were to remove or release from the ceramic dishes in which they were heated. Accordingly, after heating each composition at 90° C. for 30-60 minutes and subsequently allowing the wax compositions to cool to ambient temperature, each composition was removed from their respective ceramic dishes and scored as to the difficulty of their removal from the dish. FIGS. 2A and 2B illustrate an example of a wax melt composition that was not easy to remove and a wax melt composition that was easy to remove, respectively. Wax melt compositions that were easy to release remained intact and did not have to be scraped off in sections or portions. In some cases, the wax melt composition would easily peel off of the dish once an edge was lifted, rather than having to scrape the entire contact portion of the composition from the dish. Table 2 lists some representative examples of formulations that were easy to remove from the ceramic dishes in which they were heated and allowed to cool.

TABLE 2

| Prototype | Aerosil® R202 | Aerosil® R972 | SIPERNAT® 500LS | PG | Performance Ease of Release |
|---|---|---|---|---|---|
| 1A | 5.50% | 2.00% | | 5.00% | ++ |
| 2F | 5.50% | 1.50% | | | ++ |
| 10L | 5.50% | | | 5.00% | ++ |
| 14P | | | 5.00% | 5.00% | ++ |
| 2A | 5.50% | 0.75% | | 5.00% | + |
| 3A | | | 6.00% | | + |
| 4A | 5.50% | 1.00% | | 5.00% | + |
| 5A | 5.50% | 2.25% | | 5.00% | + |

As can be seen from Table 2, a number of inorganic thickeners improved the ease of release from the ceramic dish in which they were heated. In particular, hydrophobically-modified fumed silicas, either alone or in combination, and hydrophilic precipitated silicas (e.g. Sipernat®500LS, commercially available from Evonik) were effective at improving the ease of release of the wax compositions from the ceramic dishes. Further, a solubilizing agent, such as PG, could also be added without substantially decreasing the ease of release. Again, the weight ratio of from 2:1 to 8:1, or 2:1 to 4:1 of Aerosil® R202 to Aerosil® R972 can be effective at increasing the ease of release of wax compositions from the receptacles in which they are heated.

Example 3—Combination of Inorganic Thickeners Decreases Syneresis

As previously discussed, syneresis refers to the separation of a liquid component from the solid wax mass at ambient temperature. Accordingly, in connection with Example 1, the same wax melt compositions were evaluated for syneresis issues. More specifically, each formulation was prepared and allowed to sit for a period of time prior to heating. Each formulation was observed during that period of time to see if any fragrance or solubilizing agent would exude from the composition. In some cases, the addition of thickeners would increase the syneresis of the wax melt compositions. In some cases, the addition of thickeners would have little impact, or at least no observable impact, on the wax melt compositions. In some cases, the addition of thickeners would actually decrease the syneresis of the wax melt compositions and even increase the loading capacity of the wax melt composition (i.e. more fragrance could be added without experiencing syneresis). Table 3 illustrates a few examples of wax compositions where there was no observable effect on syneresis or where syneresis was actually decreased as compared to wax melt compositions without the addition of thickeners.

TABLE 3

| Prototype | Aerosil® R202 | Aerosil® R972 | PG | CaCO3 | Clay | Performance Syneresis |
|---|---|---|---|---|---|---|
| 1A | 5.50% | 2.00% | 5.00% | | | + |
| 4A | 5.50% | 1.00% | 5.00% | | | 0 |
| 6A | 5.50% | 1.65% | | | | 0 |
| 2D | 5.50% | 2.00% | 5.00% | | 0.50% | 0 |
| CC1 | | | 5.00% | 8.00% | 4.25% | 0 |

As shown in Table 3, a variety of inorganic thickeners appeared not to affect the syneresis of the formulations, either for better or for worse. However, some prototypes, such as prototype 1A actually decreased the syneresis of the wax melt composition and effectively increased the loading capacity of the composition. For example, prototype 1A had a 20% increase in fragrance loading capacity as compared to a wax melt composition without any additional thickeners. This would indicate that a weight ratio of Aerosil® R202 to Aerosil® R972 from about 2:1 to about 6:1 will have at least an unobservable impact on syneresis. However, where the weight ratio of Aerosil® R202 to Aerosil® R972 is from about 1:1 or 2:1 to about 3:1, the fragrance loading capacity can be increased without experiencing syneresis.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A wax melt composition, comprising:
    a wax component;
    a releasable volatile agent;
    a first inorganic thickener, wherein the first inorganic thickener is hydrophobically modified; and
    a second inorganic thickener, wherein the second inorganic thickener is hydrophilically modified.

2. The composition of claim 1, wherein the wax component includes a wax selected from the group consisting of: a vegetable wax, an animal wax, a synthetic wax, a mineral wax, a petroleum wax, and combinations thereof.

3. The composition of claim 1, wherein the wax component includes a blend of waxes.

4. The composition of claim 1, wherein the wax component includes a wax having a chain length of from about 15 to about 60 carbons.

5. The composition of claim 1, wherein the wax component is present in an amount of from about 5 wt % to about 95 wt %.

6. The composition of claim 1, wherein the releasable volatile agent is a member selected from the group consisting of: a fragrance, a pesticide, a pest repellant, an herbicide, a therapeutic agent, and combinations thereof.

7. The composition of claim 1, wherein the releasable volatile agent has a flash point of at least 140° C.

8. The composition of claim 1, wherein the releasable volatile agent is present in an amount of from about 0.01 wt % to about 30 wt %.

9. The composition of claim 1, wherein the first inorganic thickener is a silica.

10. The composition of claim 1, wherein the first inorganic thickener is present in an amount from about 0.01 wt % to about 20 wt %.

11. The composition of claim 1, wherein the second inorganic thickener is present in an amount from about 0.01 wt % to about 15 wt %.

12. The composition of claim 1, wherein the first inorganic thickener and the second inorganic thickener are present at a weight ratio of from 1:1 to 8:1.

13. The composition of claim 1, further comprising a solubilizing agent.

14. A system for volatilizing a releasable volatile agent, comprising:
a wax melt composition as recited in claim 1; and
a heat source.

15. A method of minimizing the splash potential of a wax melt composition during a heating event, comprising:
including an effective amount and weight ratio of a first inorganic thickener and a second inorganic thickener in a wax melt composition, wherein the first inorganic thickener is hydrophobically modified, and the second inorganic thickener is hydrophilically modified, and wherein the combination of the first and second inorganic thickeners reduces the splash potential of the wax composition during the heating event as compared to a wax composition without the combination of the first and second inorganic thickeners.

16. The method of claim 15, wherein the heating event comprises heating the wax melt composition to a temperature of up to 105° C.

17. The method of claim 15, wherein the effective amount of the first inorganic thickener is from about 0.01 wt % to about 20 wt %.

18. The method of claim 15, wherein the effective amount of the second inorganic thickener is from about 0.01 wt % to about 15 wt %.

19. The method of claim 15, wherein the effective weight ratio of the first inorganic thickener and the second inorganic thickener is from 1:1 to 8:1.

* * * * *